United States Patent [19]
Jacobson

[11] Patent Number: 6,099,459
[45] Date of Patent: Aug. 8, 2000

[54] MAGNETIC FIELD GENERATING DEVICE AND METHOD OF GENERATING AND APPLYING A MAGNETIC FIELD FOR TREATMENT OF SPECIFIED CONDITIONS

[76] Inventor: Jerry I. Jacobson, 2006 Mainsail Cir., Jupiter, Fla. 33477

[21] Appl. No.: 09/148,435

[22] Filed: Sep. 4, 1998

[51] Int. Cl.[7] .................................................. A61N 1/00
[52] U.S. Cl. ............................................ 600/13; 128/897
[58] Field of Search ..................... 600/9–15; 128/897–98

[56] References Cited

U.S. PATENT DOCUMENTS

| | | |
|---|---|---|
| 781,448 | 1/1905 | McIntyre . |
| 2,099,511 | 11/1937 | Caesar . |
| 2,103,440 | 12/1937 | Weissenberg . |
| 3,738,369 | 6/1973 | Adams et al. . |
| 3,890,953 | 6/1975 | Kraus . |
| 4,323,056 | 4/1982 | Borrelli . |
| 4,576,172 | 3/1986 | Bentall . |
| 4,611,599 | 9/1986 | Bentall . |
| 5,269,746 | 12/1993 | Jacobson . |
| 5,366,435 | 11/1994 | Jacobson . |

FOREIGN PATENT DOCUMENTS 0 371 504 A2  6/1990  European Pat. Off. .

OTHER PUBLICATIONS

Reuven, Sandyk, *Alzheimer's Disease: Improvement of Visual Memory and Visuoconstructive Performance by Treatment with Picotesla Range Magnetic Fields*, Intern J. Neuroscience, vol. 76 (1994), pp. 185–225.

*Primary Examiner*—John P. Lacyk
*Attorney, Agent, or Firm*—A. Jose Cortina; Kilpatrick Stockton LLP

[57] ABSTRACT

A magnetic field generator device includes a signal generator capable of operating within predetermined parameters, an attenuator is connected to the signal generator and to helmholtz coils to transmit and attenuate the signal from the generator to the coils to generate a predetermined desired magnetic field. A method of treating patients having numerous conditions provides for subjecting the patients, patient portions and/or targets therein, to the magnetic fields which are set in accordance with the characteristics of the patient, patient portion and/or target to be treated.

21 Claims, 5 Drawing Sheets

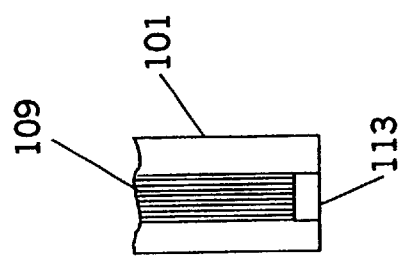
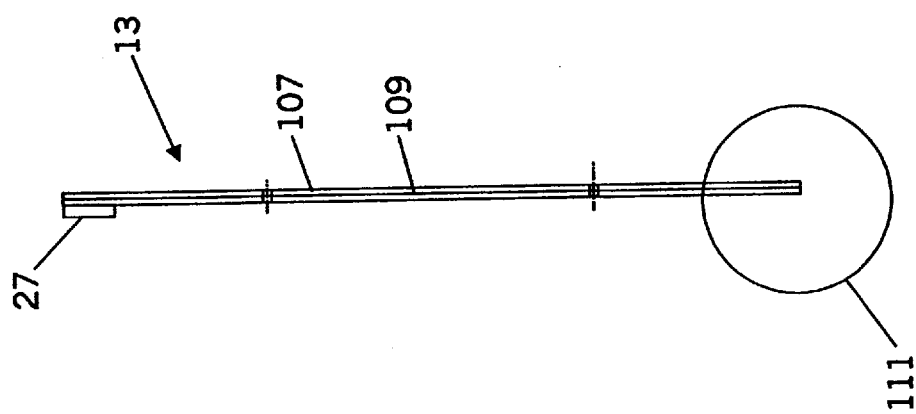
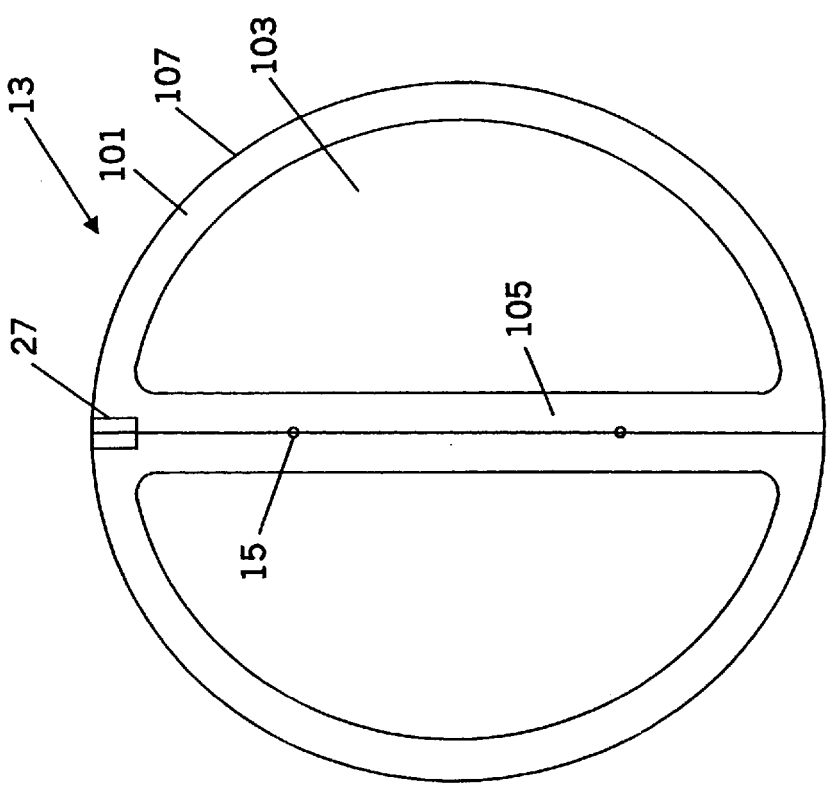

MAGNETIC FIELD GENERATING DEVICE AND METHOD OF GENERATING AND APPLYING A MAGNETIC FIELD FOR TREATMENT OF SPECIFIED CONDITIONS

CROSS-REFERENCE TO RELATED APPLICATIONS

This application is related to U.S. Pat. No. 5,269,746, and to application Ser. No. 08/440,896, filed May 24, 1995.

TECHNICAL FIELD

This invention relates to applying electromagnetic energy, and to a device for applying electromagnetic energy, to living tissues for ameliorating various conditions of such tissue, and the effects thereof in maintaining the integrity of health. In particular, the invention relates to applying a specific magnetic flux density and frequency of electromagnetic radiation, with a specifically designed device, which radiation is calculated from the mass of the target, i.e., targeted tissues and/or subcomponents thereof, to therapeutically treat a patient condition.

BACKGROUND OF THE INVENTION

In the past, a number of procedures have been described to be useful in the treatment of various diseases. Such procedures involved the employment of magnetic fields to accomplish their objectives. One example of a prior art approach is disclosed in U.S. Pat. No. 4,323,056 which teaches numerous uses of electromagnetic materials and electromagnetic fields, e.g., lasers, microwaves and radio frequency (RF) induced magnetic fields, in the therapeutic treatment of mammals suffering from various disease conditions. Typically these techniques involve ingestion of magnetic materials, for example, iron oxide in patients, in conjunction with the application of a magnetic force. The magnetic particles then become heated as a result of the coupling thereof to the magnetic field through the dielectric and hysteresis loss, with the induced heating constituting the therapeutic properties of this form of treatment. However, these prior art processes were not therapeutically successful for a number of reasons.

More recently, U.S. Pat. No. 5,269,746, teaches applying electromagnetic energy to living tissues for therapeutic purposes and in particular, to applying a specific magnetic flux density and frequency of electromagnetic radiation calculated from the mass of targeted tissues to achieve a healthful response in the tissue apart from other influences thereon. More specifically, U.S. Pat. No. 5,269,746 teaches a method for therapeutically treating patients suffering from epilepsy. The method involves calculating an electromagnetic field to be applied, by equating a gravitational energy of a target element "t" with the energy per unit charge of an electromagnetic field induced therein. The formula $mc^2 = Bvlq$ is used to thereby derive a magnetic flux density of between about $6 \times 10^{-6}$ to $6 \times 10^{-10}$ gauss. The patient is subjected to the field over an extended period of time at the flux density. The patent also teaches that the method can be used for therapeutically treating patients suffering from Parkinson's Disease.

More recently, in U.S. application Ser. No. 08/440,896, May 24, 1995, pending and now allowed, there is disclosed a method and system for applying electromagnetic energy to living tissues for ameliorating the aging process and the effects thereof. To maintain the integrity of health, and in particular, to applying a specific magnetic flux density and frequency of electromagnetic radiation calculated from the mass of the targeted tissues, with a specific patient orientation for a given amount of time. Aging is discussed as being analogous to physical development, and is discussed as producing changes in the processes of cellular genetic information transfer. Aging is thus further discussed as a slow burn of body parts. By applying the noted field, a positive effect on the aging process is observed.

These new perspectives in the radiological sciences suggest novel approaches to conditions such as cancer and AIDS, as well as numerous other conditions. The past developments present a quantum-mechanical rationale for the new perspective, and implications for radically different approaches to clinical medicine. The connection between quantum mechanics and human physiology begins with the fact that a biological system is a highly non-linear, pseudo-random, non-equilibrium complex aggregation of particles, continually rearranged by both intrinsic and extrinsic influences. Although the imagery provided by biochemical analysis has been accepted, the fact that living systems are composed of physical material particles having electromagnetic properties has often been ignored.

At the intersection of physics and human physiology is the notion, as reflected in the previously discussed patents and applications, and in numerous other articles, of Jacobson Resonance, which has explained biosystem interactions with magnetic fields.

Taking what has been known and developed in the past, there has now been developed an apparatus for generating and applying specific magnetic fields for killing viruses such as HIV (treating AIDS) and other microorganisms that are pathogenic. In addition, the device can be used for oncongenic recrystallization, and in reorientation of infectious, immunogenic RNA or DNA into normal biostructures. The device can also be used for treatment of chronic pain and neurological disorders such as multiple sclerosis, Alzheimer's, and epilepsy and Parkinson's disease. Other neurological conditions which can be treated with the device and method of the invention include chronic pain, autism, neuromuscular disorders in general, neuralgia, tics, neuropathies, central nervous system and peripheral nervous system regeneration in general (including laryngeal nerve damage preventing speech), cerebral palsy, attention deficit disability (ADD), attention deficit hyperactivity disability (ADHD), aphasia, stroke, cardiac arrhythmias and muscular dystrophy.

SUMMARY OF THE INVENTION

In accordance with one aspect of the invention, there is provided an apparatus and/or system for generating an electromagnetic field to be applied to a patient or portion of a patient such as a joint or organ, which also includes a target. The target, for purposes of this disclosure can be specific structures within the patient's body such as a virus, hormone, or can be other targets such as a portion of a patient, like an atom, electron, cytokines, neurotransmitters, genes, proteins, enzymes, protons, electrons, subatomic particles, ions such as calcium, sodium, potassium, magnesium, a cell or subcomponent thereof such as an organelle, and other like structures like histamines, leukotrines, dopamine, as will readily be apparent to those of ordinary skill in the art, as will become more readily apparent from the following detailed discussion in which numerous types of targets are described.

The device includes a signal generator for producing a signal of predetermined amplitude and of predetermined frequency to generate a desired magnetic field. The field is produced by helmholtz coils which are operatively connected to the signal generator. The signal generator is set to operate such that the field generated matches the formula $mc^2=Bvlq$, wherein m equals the mass of one of a plurality of targets to which the field is to be applied, c equals the speed of light, v is the inertial velocity of the mass, l is the length of the biosystem component thereof of the patient, i.e., a portion of the patient, such as a cell, or a joint, and q equals unity of charge. Thus, this equation is used to derive a magnetic flux density B which is generated through the helmholtz coils. An attenuator is connected for receiving the signal from the signal generator, and to drive the helmholtz coils, through connection of the helmholtz coils to the attenuator. Preferably, the generator is capable of one millivolt to ten volt amplitude at a 50 ohm load termination, and the generator is terminated into 50 ohms to maintain correct signal relationship. The attenuator is capable of attenuation from about 10 milligauss to about 1 attogauss by combining the generator range and attenuator selection ranges. The structure supporting the helmholtz coils is sized such that the helmholtz coils can range in size from 18 inches to 7 feet, depending on the target to which the field is to be applied.

In another aspect, the invention relates to a method of treating a patient comprising a target, which includes placing the target in an electromagnetic field in the apparatus and/or system of the invention. The field is generated and applied by operating the apparatus and/or system in a manner to generate a field which matches the formula $mc^2=Bvlq$, which has been previously discussed.

In a more specific aspect, the field is applied to therapeutically treat conditions such as virus infections, pathogenic organism infections, oncogenic abnormalities, infectious and immunogenic RNA or DNA, chronic pain and neurological disorders. The neurological disorders can include, for example, multiple sclerosis and Alzheimer's, as well as epilepsy and Parkinson's disease, and brain injuries like cerebral palsy as well as neuromuscular disorders like muscular dystrophy and amyotrophic lateral sclerosis (ALS). Other neurological conditions which can be treated with the device and method of the invention include autism, neuromuscular disorders in general, neuralgia, tics, neuropathies, central nervous system and peripheral nervous system regeneration in general (including laryngeal nerve damage preventing speech), cerebral palsy, attention deficit disability (ADD), attention deficit hyperactivity disability (ADHD), aphasia, stroke, cardiac arrhythmias and muscular dystrophy. In addition, the field can be applied to treat headaches and/or pain conditions of the joints.

BRIEF DESCRIPTION OF THE DRAWINGS

Having thus briefly discussed the invention the same will become better understood from the following detailed discussion taken in conjunction with the appended drawings, wherein:

FIG. 2 is a plan view of one resonator, having a helmholtz coil built therein to generate the magnetic fields in accordance with the invention;

FIG. 3 is an end view of the resonator of FIG. 2;

FIG. 4 is an enlarged partial cross-section end view of a portion of the resonator of FIG. 3;

DETAILED DISCUSSION OF THE INVENTION

Figure 1:
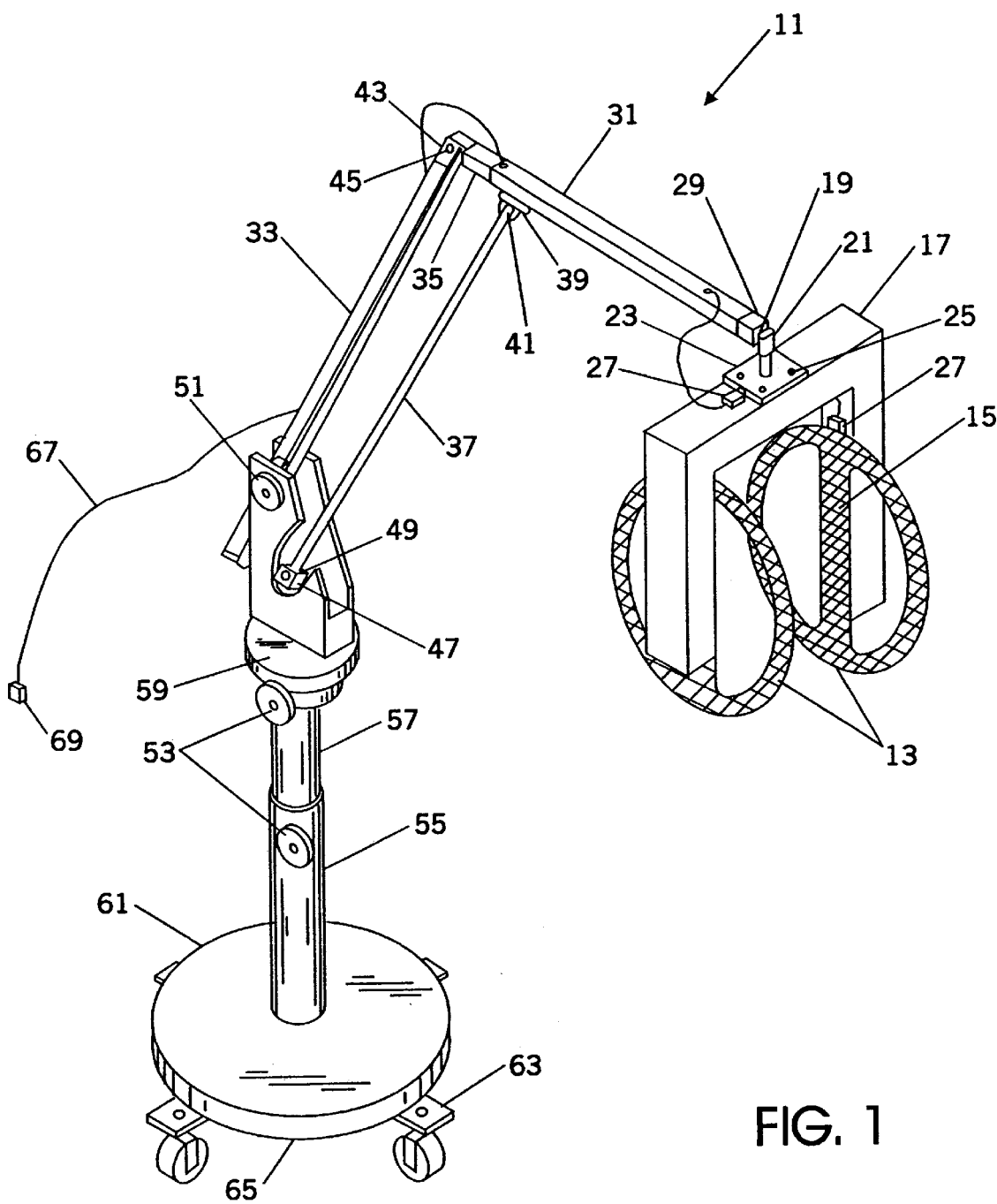
FIG. 1 is a perspective view of a portion of an apparatus of the invention, shown having a connector to be connected to a signal generator and an attenuator which are used to operate the system.

In accordance with one aspect of the invention, as shown in FIG. 1, there is provided an apparatus 11 making up part of the system of the invention, for generating a magnetic field of predetermined amplitude and frequency to treat a number of conditions. This is done by application of the magnetic field to a target in a patient or a target included in the patient or which constitutes part of a portion of a patient. In this regard, it is noted that the term "target" has been previously defined. By patient or portion of a patient is meant the whole patient or a subpart thereof such as a joint, the brain, etc.

The apparatus 11 includes two resonators in the form of disks 13 which preferably incorporate helmholtz coils as a part thereof. Mounting screws 15 are used to mount the resonators 13, which are arranged in a parallel arrangement and spaced from each other by a predetermined amount, to a mounting frame 17. The system 11 is such that the resonators 13 can be moved into a variety of positions for application of magnetic fields to different targets of a patient and the patient or subportions of the patient. A universal knob 19 serves to mount the mounting frame 17 through a universal joint knob adjustment mount 21 to end plug 29 of a first support 31.

The mount 21 is connected to a shaft plate assembly 23 which is attached to the mounting frame 17 through bolts 25. Receptacle connectors 27, as shown, are connected to the resonators 13 (not shown connected to one of the resonators 13), and are used to provide the necessary signals to the resonators 13, to generate the desired magnetic fields. Typically, the receptacle connectors 27 can be, for example, Molex 2 pin miniconnectors such as are readily commercially available.

As further shown, the first support 31 extends horizontally and terminates at an end plug 35 which is connected to an end plug 43 of a second support 33 through pin connection 45. To allow controlled movement of the resonators 13, a balance support rod 37 is provided, and connected at a support attachment 39 through a pin 41 to first support 31, and at its other end, connected to a pivoting block 59 through an end cap 47 and pin 49. The second support 33 is connected at its other end, i.e., away from support 31, to a pivot block 59 through a locking knob 51.

The pivot block 59 is connected to a vertically extending shaft 57 which is vertically moveable within a shaft support 55, and capable of being locked in different vertical positions through the use of locking knobs 53.

The shaft support 55 forms part of, and is mounted on assembly 61, which is a counter-weight to maintain the system physically stable. The counter-weight 61 is mounted on a base 63, typically of molded nylon material. A washer, bolt assembly 65 completes the assembly to provide a movable system which can be moved from one location to another through the wheels (shown but not numbered) provided with the system.

To provide a signal to the resonator discs 13, a cable 67 extends through the system frame, and terminates at a receptacle connector 69, also typically a Molex 2 pin mini connector, as previously described herein.

In this embodiment of the system 11, the resonator disks 13 are typically 18 inches in diameter and have helmholtz coils built therein to generate a field applied to specific body portions and targets of a patient. As further shown in FIGS. 2, 3 and 4, the resonator 13 is made up of a disc assembly including a disc 101 which is about one inch wide, typically made of non-metallic material, specifically non-ferrous material. For example, the disc can be made of a material such as Lexan material commercially available from Dupont Corporation. To maintain the disc 101 lightweight, a cutout area 103 is provided where no material is found. The disc 101 includes a groove 107, typically 0.02–0.05 inches wide and 0.02–0.05 inches deep, along its edge to allow copper coils to be wound thereon. Center support 105 serves to rigidify the disc 101 and serves to provide for attachment to the frame 17 through the mounting screws 15. In the embodiment of FIG. 2, the receptacle connector 27 is showed mounted thereon.

As further shown in FIG. 3, wire coils 109 are shown wound into the groove 107. Preferably, the wire coils 109 are copper, although other equivalent non-ferrous materials can be used in place thereof. As further shown in the circled portion 111, illustrated in enlarged form in FIG. 4, the wire coils 109 are covered, as shown in the cross-sectional enlarged view of FIG. 4, with epoxy, which is sanded smooth.

Figure 5:
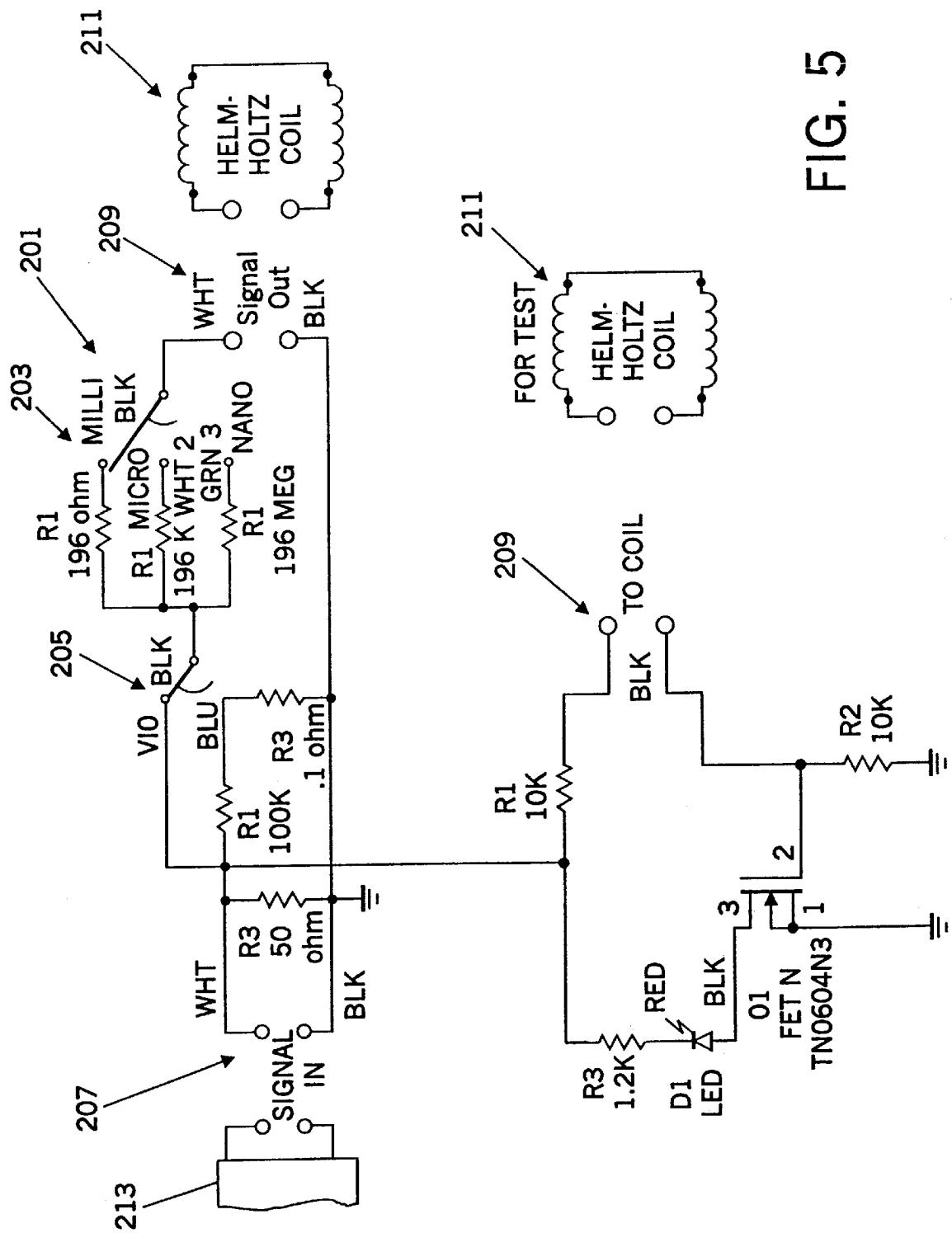
FIG. 5 is a circuit diagram showing an example of a signal generator, an attenuator and resonators (helmholtz coils) interconnected for operation in accordance with the invention.

As further shown in FIG. 5, the system 11 is driven by a signal generator in cooperative operation with the attenuator. In FIG. 5, the signal generator 213 and attenuator 201 are shown in circuit schematic form. Specifically, FIG. 5 shows a signal generator 213 connected at connection 207 to an attenuator 201. The attenuator 201 includes a rotary switch 203 for impedance matching, for example for switching for milli ($10^{-3}$) micro ($10^{-6}$), and nano ($10^{-9}$) selections. A toggle switch 205 serves to induce an additional micro ($10^{-6}$) level of attenuation to the signal levels. This provides for a total of $10^{-15}$ signal attenuation. All interconnections are made through standard BNC type connectors. The resonator 13 coils 211 are never, under any circumstances, to be connected directly to the signal generator 213, as magnetic fields in the gauss range are then possible, depending on the generator settings.

Figure 6:
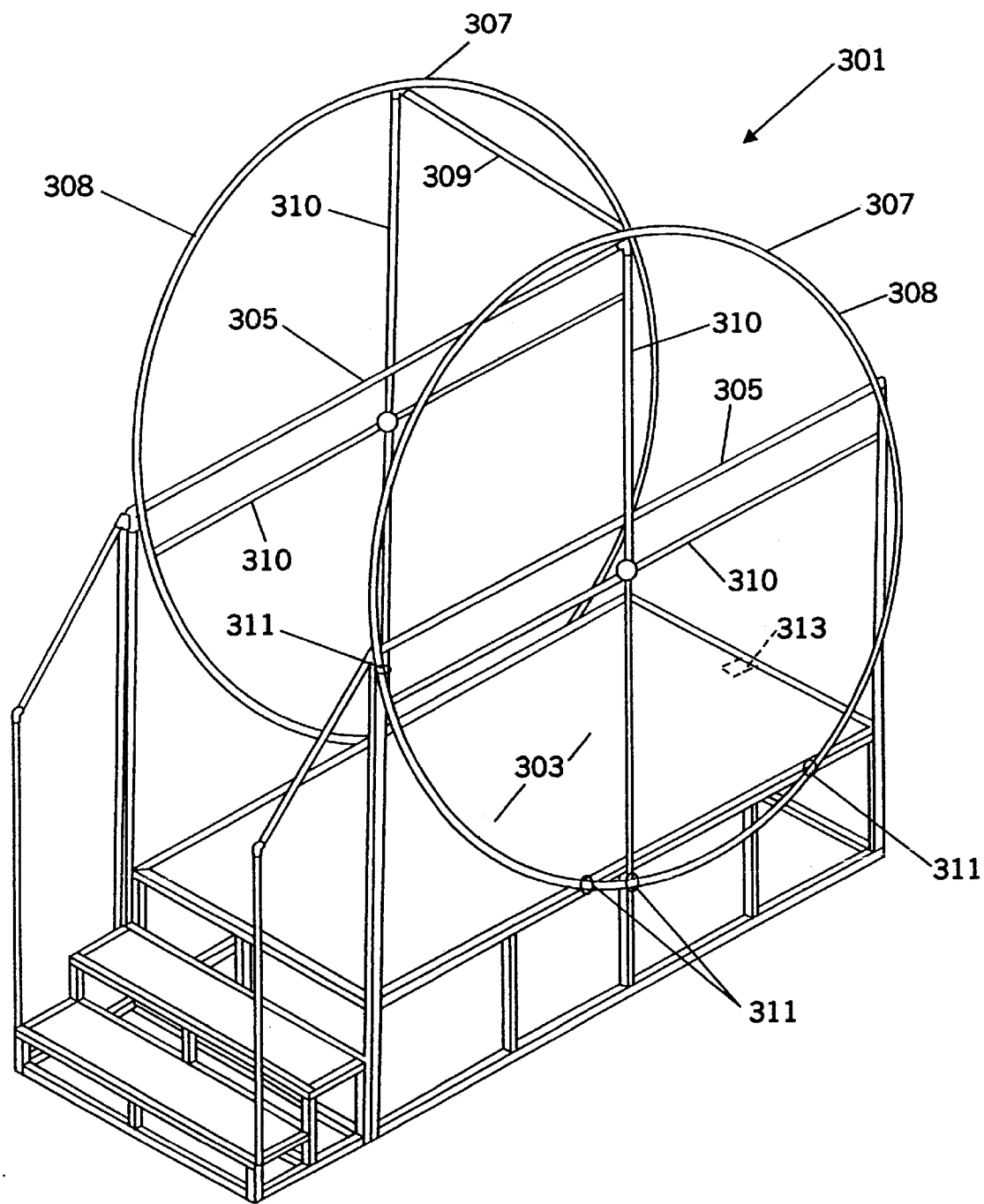
FIG. 6 is a perspective view of an alternative embodiment of the system in accordance with the invention, shown with larger helmholtz coils support structures.

In the system 11 of FIGS. 1–4, preferably the resonator discs 13 are eighteen inches in diameter. An alternative embodiment of the invention is shown in FIG. 6 as apparatus 301. The system 301 includes a platform 303 with steps for patients to walk up and mount the platform 303. Handrails 305 serve to provide stability for the patient. The resonators 307 in this case are solid discs with the wire wound around an end groove 107, substantially as shown in FIGS. 3 and 4. In fact, in this embodiment of FIG. 6, portions of the disc 307 are identical to that of the embodiment of FIGS. 1–4, as specifically shown in FIGS. 3 and 4. Because of the size of the discs 307, a support rod 309 connects one disc 307 to the other disc 307 to provide stability, and the discs 307 are mounted onto the platform through disc supports 311. A field magnetometer 313 is provided to measure field intensity during treatment. As further shown in FIG. 7, the disc is made up of an outer copper coil support 308, supported by crossbars 310, and is also preferably made of Lexan material or other non-ferrous material as is done with the embodiment of FIGS. 1–4. Alternatively, the disc 307 can be solid throughout with the groove 107 cut into its outer edge.

Figure 7:
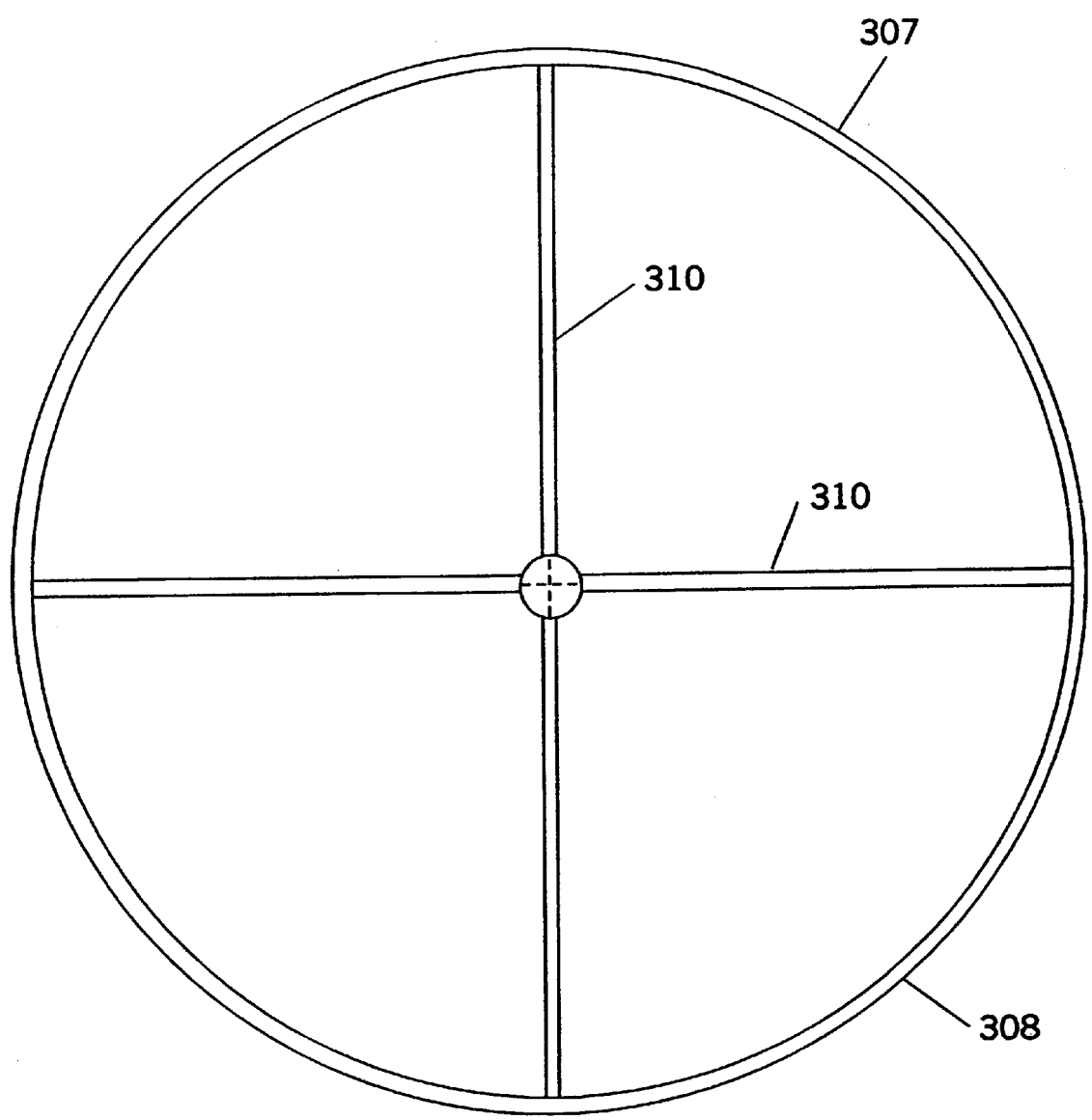
FIG. 7 is a plan view of the helmholtz coil support structure such as is used in the embodiment of FIG. 6.

As previously described with respect to FIGS. 1–4, the system of FIGS. 6 and 7 also includes a signal generator 213, an attenuator unit 201, and a set of coils 211, i.e., a pair, each one being spaced from the other by a predetermined amount. No ferrous metals are utilized in the construction of the resonators 13, 307, and the mounting and support system.

In the case of the embodiment of FIG. 1, bolts on each of the wheels and locking knobs, 51–53 are of ferrous material due to strength requirements. However, field uniformity is not affected by such a small amount of ferrous metal. The signal generator 213 is selected to produce the precise amplitude and frequency for the desired magnetic field. Typically, the generator is an HP (Hewlett Packard) 3325 B signal generator. The generator 203 is a precision device, capable of DC to 20 MHz frequency generation in square, sinusoidal, and triangle wave forms. The generator 203 is capable of one millivolt to ten volts amplitude generation into a 50 ohm load termination. The generator must be terminated into 50 ohms at all times in order to maintain correct signal relationships. The attenuator 201 uses the signal produced by the generator 213 to drive the coils 24 of the resonators 13, 307.

The circuitry (FIG. 5) of the attenuator 201 is custom designed to provide impedance matching to the generator 213, and selectable attenuation of the signal. The attenuation ranges from 10 milligauss to 1 attogauss by combining the generator range and the attenuator selection ranges. Thus, the range of flux density achieved can range from about 10 milligauss to about 1 attogauss. The field generated is of multiple harmonic frequencies from DC to about 1000 Hz, which is derived from the equation $F=qB/2\pi m_q$ where q is the charge of an ion such as calcium ion, or a charged species like a proton or electron, or equal to unity (e.g., for proteins and DNA), F is the frequency, B is the flux density and in this $m_q$ is the mass of the charged species. Circuitry within the unit provides for continuity verification after assembly of the system to confirm a complete circuit for the signal generator 213. The unit has two switches, one rotary switch 203, as previously discussed for impedance matching for milli ($10^{-3}$), micro ($10^{-6}$), and nano ($10^{-9}$) selections, and one toggle switch 205 for inducing an additional micro ($10^{-6}$) level of attenuation to the above signal levels. This provides for a total of $10^{-15}$ signal attenuation. As previously noted, all interconnections are made through standard BNC type connectors.

The magnetic fields are produced by the simplified helmholtz coils 211, as incorporated into the resonators 13, 307. In the embodiment of FIG. 1, the resonators 13 are eighteen inches in diameter, with a separation from each other of 9 inches. The helmholtz coils 211 incorporated into the resonators 13 are comprised of five turns of number 37 gauge wire around an eighteen inch disc made of one-quarter inch, for example, Lexan material. The discs have a 0.020–0.050 by 0.020–0.050 inch groove in the edge, with an epoxy filler 113 used to cover the windings 109. The resonator 13 is terminated with a black gloss enamel finish. Internal areas 103 of the discs resonator 13 have been removed for weight reduction. As noted previously, coil 211 interconnections are made through two-pin friction fit connectors such as Molex connectors. In the case of the resonator 307 of FIGS. 6 and 7, they are preferably 7 feet in diameter and spaced about 3.5 feet apart.

As shown in FIG. 1, the apparatus 11 provides the correct separation and mounting for the resonators 13 coils 211. The apparatus 11 is capable of 180° rotation and 90° pivoting. The apparatus 11 is fabricated from preferably, in the case of the system of FIG. 1, two inch PVC tubing with reinforced corners, and backing blocks for additional strength and rigidity. All mounting hardware are nylon ¼-20 screws.

The apparatus 11 also includes, as shown, a support stand including a counter weight 61 and washer bolt assembly 65 which, with the shaft support 55, and locking knobs 53, provides 360° rotation of the apparatus 11, with vertical and horizontal movement of approximately three feet, and the ability to secure the apparatus 11 in any position. This provides extreme versatility in positioning and securing the apparatus 11. The support stand of the apparatus 11 is fabricated from PVC with brass hardware for interconnecting its subassemblies.

With respect to the base of the system, the counter weight 61 preferably weighs approximately 65 pounds. The base of the system is made of high impact nylon and will support in excess of 250 pounds of weight with 360° swivel capability. The counter weight 61 is made from PVC and filled with 50 pounds of sand.

In operation, verification of the signal generator 213 and attenuator 201 circuitry is performed by applying a fixed five volt signal to the attenuator 201 input and plugging the coils 211 across the coil 211 test output shown in FIG. 5. An LED (not shown) on the signal generator 213 will illuminate, indicating a complete circuit has been obtained. The generator 213 signal is then returned to zero voltage and the system is ready for use.

The magnetic field is characterized for each set of coils 211 fabricated for the helmholtz configuration. The field characterization provides a pseudo three dimensional relationship within the coil 211 area. Each helmholtz coil configuration was characterized with 27 data points, 9 points on each of three vertical plane (left, right, and center). The characterizing of the magnetic field indicated the intensity at a predetermined location with the coil field area.

After characterizing the magnetic field, the data was averaged over the area of the three vertical planes and compared to the generator 213 settings to determine the field correlation. The correlation verified the field intensity levels to the generator's 213 settings. The field correlation to the generator 213 is such that, a one volt signal is equal to one milligauss. This relationship is based on a one volt signal from the generator 213 and the attenuator 201 set in the milligauss range.

This was done in a similar manner for the embodiment of FIGS. 6 and 7, which in this case provides for seven foot resonators 307.

Referring now to the use of the apparatus 11, 301 of the invention, it is used on the basis that it is possible to control the effects of externally sourced magnetic fields on the body. It is possible to vibrate molecules by hitting them with resonance energy that communicates through frequency and amplitude. Amplitude refers to the intensity of flux density of the field. Amplitudes that are physiologic may be drawn to correlate with known molecular vibrational frequency through the previously explained Jacobson resonance. In Jacobson resonance, as previously discussed, $mc^2=Bvlq$, where m is mass, c is the velocity of light, B is flux density, v is inertial velocity, l is length and q is charge normalized to a single coulomb. Therefore, frequency is equal to flux density times unit charge, divided by mass and adjusted by a changing biosystem.

In the case of the method of the invention as implemented through the system previously described, Jacobson resonance provides using the following continuous functions:

$$\frac{c}{qv} \cdot Smc \cdot dl = \left(\frac{aB3}{ay} - \frac{aB2}{az}\right)i + \left(\frac{aB1}{az} - \frac{aB3}{2x}\right)j + \left(\frac{aB2}{2x} - \frac{aB1}{ay}\right)k \quad (18)$$

The foregoing expression represents the equivalence of the intrinsic energy of a mass, and the interaction energy resulting from an interaction of a body and magnetic flux or magnetic field vectors. Eigen values and eigen vectors must be analyzed in conjunction with parameters of biosystems. Algebraic descriptions of nature approximate in a general sense, while the calculus applies to details.

Thus, in accordance with the invention, resonance frequency and sharpness of resonance is essential in a driven vibrating system. When a vibrating system is sharply resonant, careful tuning is required to obtain the resonance condition. Thus, it becomes apparent from the following description and discussion that the effects of Jacobson magnetic resonance can be used in accordance with the system of the invention for different purposes.

An eighteen inch resonator is good for specific types of localized pain. A seven foot resonator can treat anything. As will become readily apparent to those of ordinary skill and the art, intermediate sizes can also be provided, for example, a three foot resonator could be used for lower back pain. The system in accordance with the invention is therefore, used in accordance with the method for a number of different conditions, particularly pain and neurological disorders. In addition, it is also believed that the system can be used to kill viruses, and other microorganisms that are pathogenic. It can be used to cause oncongenic recrystallization, and reorientation of infectious, immunogenic RNA or DNA into normal biostructures. Treatment of chronic pain and neurological disorders like multiple sclerosis and Alzheimer's disease, as well as epilepsy and Parkinson's disease, and cerebral palsy and amyotrophic lateral sclerosis (ALS) can be achieved using multiple resonant harmonic frequencies from milligauss to the $10^{-21}$ gauss.

In terms of specific field applications, typical applications of frequencies are shown in the following tables. Specifically, the following tables indicate preferred settings and general protocols for generating magnetic fields to be applied to different types of targets/conditions in a patient and/or patient portions. The tables are separated as indicated by gauss settings for different conditions as indicated.

The amplitude is set at the signal generator 213 of the system shown in FIG. 5. The frequencies indicated are achieved by appropriate settings at the attenuator 201 of the system.

TABLE I

Microgauss Settings

| Target | Amplitude (volts) | Frequency in Hz, electrons ($e^-$) | Frequency in Hz, protons ($p^{30}$) |
|---|---|---|---|
| Virus (whole) | 10 | 279.9 | .15 |
| Virus (whole) | 9 | 251 | .135 |
| Virus (whole) | 8.8 | 246 | .132 |
| Virus (whole) | 7 | 197 | .1 |
| Interferon | 6.35 | 178 | .095 |
| Growth factors | 5.15 | 144 | .077 |
| Enzymes | 4.55 | 126 | .067 |
| Motor proteins | 3.42 | 95.8 | .0513 |
| Calmodulin | 2.83 | 78 | .042 |
| NGF | 2.54 | 71 | .038 |
| Kinesine, antibodies | .997 | 27.9 | .015 |
| MAP | .84 | 23.5 | .0126 |
| Spectrin and brain specific fodrin | .7 | 19.6 | .01 |
| Beta spectrin | .654 | 18.2 | .01 |
| Neurofilaments | .57 | 15.99 | .0085 |
| Neurofilaments | .457 | 12.8 | .0069 |
| Oncogenes, homeoboxes | .343 | 9.59 | .0051 |
| Homeoboxes | .274 | 7.66 | .0041 |
| Neural filaments, | .2 | 5.71 | .003 |

TABLE I-continued

Microgauss Settings

| Target | Amplitude (volts) | Frequency in Hz, electrons (e$^-$) | Frequency in Hz, protons (p$^{30}$) |
|---|---|---|---|
| hemoglobin | | | |
| Hemoglobin | .192 | 5.36 | .0028 |
| Viral proteins | .175 | 4.9 | .0028 |
| Viral proteins | .162 | 4.53 | .00243 |
| Interferon | .115 | 3.15 | .0017 |
| GAP (tau), growth associated protein | .126 | 3.5 | .002 |
| BGF, tubulin | .15 | 4.2 | .0023 |
| Leukotrine | .1 | 2.798 | .0015 |
| PDGF, interferon | .09 | 2.52 | .00135 |
| PDGF, interferon | .085 | 2.38 | .00127 |
| PDGF, interferon | .081 | 2.27 | .00127 |
| NGF | .081 | 2.1 | .00127 |
| Dimers of light polypeptide chains, NGF | .0667 | 2.01 | .00127 |
| NGF | .06 | 1.68 | .00127 |
| Melatonin | .05 | 1.4 | .00127 |
| Calmodulin (DNA repair) | .04 | 1.12 | .00127 |
| Serotonin, hormones, epi | .035 | .976 | .0005 |
| Hormones,epi | .02 | .56 | .0005 |
| Hormones, epi | .012 | .336 | .0005 |

In the following tables, protonic frequencies are for all practical purposes unchanging and set, for example; at 0.0005 Hz. other values can be used as will be readily apparent. Targets in patients are identified in the following table.

TABLE II

Nanogauss Settings

| Target | Amplitude | Frequency in Hz, electron (e$^-$) |
|---|---|---|
| Hormones, epi | .1 | .28 |
| Hormones, epi | 8.6 | .24 |
| Hormones, epi | 7.8 | .218 |
| NGF (solar) | 5.9 | .16 |
| NGF (solar) | 3.5 | .098 |
| H$_2$O | 2.99 | .09 |
| Leukotrines | 1.76 | .021 |
| Leukotrines | 1.47 | .041 |
| Leukotrines | 1.195 | .033 |
| Leukotrines | .895 | .025 |
| Melatonin | .667 | .02 |
| Serotonin | .4937 | .0138 |
| EPI | .431 | .012 |
| Dopamine | .347 | .097 |
| Histamine | .316 | .0885 |
| Histamine | .095 | .001 |
| Histamine | .0538 | .0015 |
| Water | .046 | .001288 |

TABLE III

Microgauss Settings

NOTE: The patient portion in all the following is the brain for conditions of Parkinson's Disease and multiple sclerosis. The time of application of the field is set at about thirty (30) to about forty (40) minutes.

| Amplitude (volts) | Frequency in Hz, electrons (e$^-$) |
|---|---|
| .077 | 2.17 |
| .076 | 2.13 |
| .075 | 2.1 |
| .074 | 2.072 |

TABLE III-continued

Microgauss Settings

NOTE: The patient portion in all the following is the brain for conditions of Parkinson's Disease and multiple sclerosis. The time of application of the field is set at about thirty (30) to about forty (40) minutes.

| Amplitude (volts) | Frequency in Hz, electrons (e$^-$) |
|---|---|
| .073 | 2.044 |
| .072 | 2.016 |
| .071 | 1.988 |
| .07 | 1.96 |
| .069 | 1.932 |
| .068 | 1.904 |
| .0667 | 1.8667 |
| .066 | 1.864 |
| .065 | 1.83 |
| .064 | 1.8 |

TABLE IV

Microgauss Settings

NOTE: The patient portion in all the following is a joint in which pain is felt, including as a result of bone conditions. The total time of application of the field is set at about fifty-six (56) minutes in increments of time at the volts and frequency indicated below.

| Amplitude (volts) | Frequency in Hz, electrons (e$^-$) | Time |
|---|---|---|
| .274 | 7.7 | 6 |
| .2 | 5.6 | 10 |
| .15 | 4.1 | 10 |
| .126 | 3.5 | 6 |
| .09 | 2.5 | 6 |
| .078 | 2.1 | 6 |
| .05 | 1.4 | 6 |
| .034 | .971 | 6 |

TABLE V

Microgauss Settings

NOTE: The patient portion in all the following is the brain in which a migraine or cluster headache is felt. The time of application of the field is set at about forty (40) minutes in the following time increments.

| Amplitude (volts) | Frequency in Hz, electrons (e$^-$) | Time |
|---|---|---|
| .035 | .98 | 4 |
| .034 | .952 | 4 |
| .033 | .92 | 4 |
| .032 | .896 | 4 |
| .031 | .87 | 4 |
| .03 | .84 | 4 |
| .029 | .81 | 4 |
| .028 | .784 | 4 |
| .027 | .75 | 4 |
| .026 | .73 | 4 |

TABLE VI

Microgauss Settings

NOTE: The patient or patient portions in all the following are mice with nerve damage. The field is applied to achieve nerve regeneration.

| Amplitude (volts) | Frequency in Hz, electrons (e$^-$) |
|---|---|
| .10 | .280 |
| .10 | .15 |
| 2.54 | .71 |

TABLE VI-continued

Microgauss Settings
NOTE: The patient or patient portions in all the following are mice with nerve damage. The field is applied to achieve nerve regeneration.

| Amplitude (volts) | Frequency in Hz, electrons (e$^-$) |
|---|---|
| 1.3 | 36 |
| .997 | 27.9 |
| .825 | 23 |
| .7 | 19.6 |
| .57 | 16 |
| .46 | 12.8 |
| .34 | 9.6 |
| .27 | 7.6 |
| .175 | 5.4 |
| .15 | 4.1 |
| .126 | 3.5 |
| .09 | 2.5 |

In addition to the above defined protocols as set forth in the tables, specific examples are set forth below of field applications to specific conditions in tests conducted on a number of patients. In particular, the device of the invention and the methods were used to treat knee pain, broken down into the following categories and diagnoses as set forth in the following examples. Amplitude and frequency are indicated in the tables of the examples.

EXAMPLE 1

The causes of knee pain are broken down as follows, and the treatment conducted is indicated:

1. Musculoskeletal, including degenerative (osteoarthritis), torn meniscus and gouty arthritis. Treatment was conducted by applying a field with the system of FIG. 1 for a total of 54 minutes in the following varying amplitudes and frequencies, in the following time subperiods.

| Amplitude (volts) | Frequency (Hz) | Time (mins) |
|---|---|---|
| 0.274 | 7.7 | 6 |
| 0.2 | 5.6 | 10 |
| 0.15 | 4.1 | 10 |
| 0.126 | 3.5 | 6 |
| 0.09 | 2.5 | 6 |
| 0.078 | 2.1 | 6 |
| 0.05 | 1.4 | 6 |
| 0.034 | 0.976 | 6 |

2. Neurogenic, including lumbar radiculopathy (sciatica), peripheral neuralgia, compression neuropathy. Treatment was conducted by applying a field with the system of FIG. 1 for a total of 52 minutes in the following varying amplitudes and frequencies for an initial 30 minute subperiod and subsequent one minute subperiods.

| Amplitude (volts) | Frequency (Hz) | Time (mins) |
|---|---|---|
| .037 | .976 | 30 |
| .077 | 2.17 | 1 |
| .076 | 2.13 | 1 |
| .075 | 2.13 | 1 |
| .074 | 2.072 | 1 |
| .073 | 2.044 | 1 |
| .072 | 2.016 | 1 |
| .071 | 1.988 | 1 |
| .07 | 1.96 | 1 |
| .069 | 1.932 | 1 |
| .068 | 1.904 | 1 |
| .067 | 1.867 | 1 |
| .066 | 1.83 | 1 |
| .034 | 0.976 | 1 |

If the patient is still suffering pain, an additional signal of 0.274 volts at 7.7 Hz is added for an additional ten (10) minutes.

3. Inflammatory, including osteoarthritis, was treated. Treatment was conducted by applying a field with the system of FIG. 1 for a total of 42 minutes in the following varying amplitudes and frequencies in six minute subperiods.

| Amplitude (volts) | Frequency (Hz) | Time (mins) |
|---|---|---|
| 0.2 | 5.6 | 6 |
| 0.15 | 4.1 | 6 |
| 0.126 | 3.5 | 6 |
| 0.09 | 2.5 | 6 |
| 0.07 | 2.1 | 6 |
| 0.05 | 1.4 | 6 |
| 0.034 | .0976 | 6 |

In all cases of treatments for the above conditions, following the protocols indicated, improvement of each condition was observed. In this case l in the equation $mc^2=Bvlq$ is the length of the whole organism or patient, or a body part such as a joint, or cell, or any other subcomponent of the body. In the equation m is generally a critical molecule in the body part or associated with the function of the body part such as a critical molecule, atom or subatomic particle, etc.

EXAMPLE 2

In a further example, a patient having knee pain was seated. The resonators 13, in this case the eighteen inch embodiment, were placed longitudely with respect to the leg with the knee being placed between the two resonators 13. The amplitude was set at 0.20 volts and the frequency was set at 5.6 Hz. The system was turned on for 42 minutes. At the end of the session, the patient was reevaluated and entries made in both the patient log and the technician log. Again, as in the case with Example 1, improvement and reduction of pain was observed.

EXAMPLE 3

To further support the observations of improvement through the use of the system of the invention, the effects of Jacobson resonance were studied in vitro on sciatic nerve for mice. Aseptic procedures were used to dissect four pieces of bilateral nerves. The nerves were maintained in a culture medium. Two of the nerve pieces served as the control, and the other two were exposed to Jacobson resonance for a period of 35 minutes each day. The protocol followed is set forth in the following Table A.

TABLE A

AMPLITUDES AND FREQUENCIES OF MAGNETIC FIELDS*

| Critical Molecules** | Amplitude (Gauss) | Frequency (Hertz) |
|---|---|---|
| Spectrin; Brain Specific Fodrin | $1 \times 10^{-5}$ | .015 |
| Hemoglobin | $2.5 \times 10^{-6}$ | 71.0 |
| Interferon; Leukotrines; Platelet Derived Growth Factor (PDGF) | $1.3 \times 10^{-6}$ | 36.0 |
| Nerve Growth Factor (NGF); Kinesine | $9.97 \times 10^{-7}$ | 27.9 |
| Microtubule Associated Protein (MAP) 2a. 2b | $8.25 \times 10^{-7}$ | 23.0 |
| Melatonin; spectrin; Brain Specific Fodrin | $7 \times 10^{-7}$ | 19.0 |
| Neurofilaments; Calmodulin | $5.7 \times 10^{-7}$ | 16.0 |
| Epinephrine; Serotonin | $4.6 \times 10^{-7}$ | 12.8 |
| Homeoboxes | $3.4 \times 10^{-7}$ | 3.6 |

TABLE A-continued

AMPLITUDES AND FREQUENCIES OF MAGNETIC FIELDS*

| Critical Molecules** | Amplitude (Gauss) | Frequency (Hertz) |
|---|---|---|
| Dopamine; Norepinephrine; Neurofilaments | $2.7 \times 10^{-7}$ | 7.6 |
| Microtubule Associated Protein (MAP); Calcium; Iron | $1.75 \times 10^{-7}$ | 5.4 |
| Spectrin; Potassium; Chlorine; Bone Growth Factor (BGF) | $1.5 \times 10^{-7}$ | 4.1 |
| Tubulin; Homeoboxes | $1.26 \times 10^{-7}$ | 3.5 |
| Interferon; Serotonin; Platelet Derived Growth Factor (PDGF) | $9 \times 10^{-7}$ | 2.5 |

*Nerves were exposed to each combination of amplitude and frequency in the order in which they appear in Table A for 2.5 min., for a total of 35 min., for five days
**The masses of the named critical molecules were used in calculating the amplitude and frequency of the desired magnetic fieid.

At the end of five days, dimensional studies of the nerve pieces showed that the treated nerve pieces showed significant growth in length and thickness. Histological studies under light microscope (40 fold magnification) revealed lack of growth and repair in the control group. In contrast, the treated group showed significant growth and repair indicated by the increase number and size of axons surround by normal myelin sheaths. Electronmicroscopy (40,000 fold magnification) studies showed distorted myelin sheaths in the control group. Furthermore, unmyelinated fibers with sparse, irregularly arranged microtubules were seen. Mitochondria in the control group cross sections had an inactive, orthodox conformation and the Schwann cells were swollen with vacuoles. The cross sections of the treated nerves showed normal myelin sheaths as well as normal distribution of microtubules and microfilaments. Schwann cells showed normal configuration and mitochondria were of condensed conformation indicative of anabolic activity. These observations showed that exposure to Jacobson resonance sustains the normal sub-cellular structure of the nerve cells as well as promotes repair and growth.

This study was replicated using 24 more nerve sections, most from sciatic nerves. All nerve sections showed growth. The initial study was thus confirmed. The following table documents what was observed.

TABLE B

COMPARISON OF MICROSCOPIC OBSERVATIONS OF EXPOSED AND UNEXPOSED NERVE TISSUE

| Nerve Cell Organelle | Control (Unexposed) | Experimental (Exposed) |
|---|---|---|
| Axons | Without or sparse microtubules (L.M.)* | Dispersed and normal; surrounded by endoneurium (L.M.)* |
| Myelin Sheath | Distorted with irregular lamellar arrangement and retracted from axonal membrane (L.M.)* | Normal and attached to Schwann cells (L.M.)* |
| Microtubules and Microfilaments | Aggregated and irregular (E.M.)** | Normal (E.M.)** |
| Schwann Cells | Contained a large number of vacuoles (E.M.)** | Nonnal (E.M.)** |
| Mitochondria | Swolten, orthodox conformation (inactive) (E.M.)** | Condensed conformation (Active) (E.M.)** |

In addition to the protocols for specific conditions set forth in Tables I–VI previously set forth, additional protocols for other conditions are set forth in the following additional tables. Where actual clinical testing and results was done and achieved, it is so indicated.

TABLE VII

The following protocol is followed for amyotrophic lateral sclerosis, strokes and multiple sclerosis to achieve basic nerve regeneration. This was done at microgauss settings.

| Amplitude (volts) | Frequency (Hz) | Time (mins) |
|---|---|---|
| 1.0 | 27.9 | 1–3 |
| .82 | 23 | 1–3 |
| .72 | 20.16 | 1–3 |
| .654 | 18.2 | 1–2 |
| .57 | 16.0 | 1–2 |
| .457 | 12.8 | 1–2 |
| Rest Period | | 3 |
| .343 | 9.59 | 2–3 |
| .274 | 7.68 | 5–6 |
| .200 | 5.6 | 4–5 |
| .175 | 4.9 | 2–3 |
| Rest Period | | 6 |
| .150 | 4.2 | 6–7 |
| .126 | 3.5 | 5–6 |
| .115 | 3.15 | 1–2 |
| .090 | 2.52 | 4–5 |
| .075 | 2.1 | 8–10 |

TABLE VII-continued

The following protocol is followed for amyotrophic lateral sclerosis, strokes and multiple sclerosis to achieve basic nerve regeneration. This was done at microgauss settings.

| Amplitude (volts) | Frequency (Hz) | Time (mins) |
|---|---|---|
| Rest Period | | 10 |
| .050 | 1.4 | 3–4 |
| .038 | 1.1 | 3–4 |
| .034 | .976 | 10–12 |
| .030 | .84 | 2–3 |
| .025 | .7 | 2–3 |
| .020 | .56 | 2–3 |

TABLE VIII

The following protocol was followed for the case of a patient having cerebral palsy who was forty-two (42) inches tall. This was done at microgauss settings as set forth below. After treatment, marked improvement in symptoms was observed.

| Amplitude (volts) | Frequency (Hz) | Time (mins) |
|---|---|---|
| .37 | 10 | 2.5 |
| .32 | 8.9 | 2.5 |
| .24 | 6.7 | 2.5 |
| .14 | 3.92 | 2.5 |
| .12 | 3.36 | 2.5 |
| .08 | 2.24 | 2.5 |
| .064 | 1.8 | 2.5 |
| .034 | .976 | 30 |

TABLE IX

| Amplitude (volts) | Frequency (Hz) | Time (mins) |
|---|---|---|
| The following protocol is followed for Parkinson's disease, multiple sclerosis, Alzheimer's disease and stroke. This is done at microgauss settings using the eighteen inch resonators. | | |
| .077 | 2.17 | 3.5 |
| .076 | 2.13 | 3.5 |
| .075 | 2.1 | 3.5 |
| .074 | 2.07 | 3.5 |
| The resonators are then rotated front to back and the patient subjected to a rest period of about 20 to about 30 minutes. Treatment is then continued as follows: | | |
| .075 | 2.1 | 3.5 |
| .074 | 2.07 | 3.5 |
| .073 | 2.04 | 3.5 |
| .072 | 2.02 | 3.5 |

TABLE X

| Amplitude (volts) | Frequency (Hz) | Time (mins) |
|---|---|---|
| The following protocol is followed for muscle spasms, tendonitis (elbow) and cramps. The eighteen inch resonators are used at microgauss settings | | |
| .034 | .952 | 20 |
| .274 | 7.7 | 15 |
| .2 | 5.6 | 10 |
| .034 | .952 | 5 |
| If necessary, the following additional intervals of treatment are provided. | | |
| .15 | 4.2 | 10 |
| .034 | .952 | 20–30 |

TABLE XI

The following protocol was followed for a patient having laryngeal nerve damage which caused an inability to speak. The seven foot resonators were used at microgauss settings. After treatment, the patient was able to speak

| Amplitude (volts) | Frequency (Hz) | Time (mins) |
|---|---|---|
| .034 | .976 | 3 |
| .075 | 2.1 | 17 |
| .034 | .976 | 5 |
| .457 | 12.8 | 5 |
| .038 | 1.1 | 4 |
| .7 | 19.6 | 3 |
| .034 | .976 | 5 |
| .274 | 7.7 | 3 |
| .2 | 5.6 | 2 |
| .034 | .976 | 5 |
| .15 | 4.2 | 5 |
| .034 | .976 | 10 |

Having thus described the invention, the same will become better understood from the appended claims which are intended to set forth the invention in a non-limiting manner.

What is claimed is:

1. An apparatus for generating an electromagnetic field to be applied to a patient comprising a target, for treating specified conditions, the apparatus comprising:

a signal generator for producing a signal of predetermined amplitude and predetermined frequency to generate a desired magnetic field which is produced by helmholtz coils operatively connected thereto, said signal generator being set such that the field generated matches the formula $mc^2 = Bvlq$, wherein m equals a mass of one of a plurality of targets to which the field is applied, c equals the speed of light, v equals inertial velocity of said mass, l equals the length of the patient or portion thereof, and q equals unity of charge, to thereby derive a magnetic flux density (B);

an attenuator connected for receiving said signal from said signal generator and to drive helmholtz coils to which the attenuator is connected; and helmholtz coils connected to said attenuator for being driven by said attenuator in a manner to generate said magnetic field.

2. The apparatus of claim 1 wherein said generator is capable of DC to 20 MHz frequency operation in square, sinusoidal and triangle waveforms.

3. The apparatus of claim 2 wherein said generator is capable of 1 millivolt to 10 volts amplitude at a 50 ohm load termination, and wherein said generator is terminated into 50 ohms to maintain correct signal relationship.

4. The apparatus of claim 2 wherein said attenuator is capable of an attenuation range from about 10 milligauss to about 1 attogauss by combining the generator range and attenuator selection ranges.

5. The apparatus of claim 4 wherein said attenuator has a rotary switch for providing milli ($10^{-3}$), micro ($10^{-6}$) and nano ($10^{-9}$) levels of attenuation, and a toggle switch for providing an additional micro ($10^{-6}$) level of attenuation to the rotary switch controlled attenuation, to provide a total of $10^{-5}$ signal attenuation.

6. The apparatus of claim 1 wherein said helmholtz coils are made with no ferrous metals incorporated therein.

7. The apparatus of claim 1 wherein said helmholtz coils comprise two coils, are about eighteen inches in diameter, and are spaced from each other by about nine inches.

8. The apparatus of claim 1 wherein said helmholtz coils comprise two coils, are about seven feet in diameter, and are spaced from each other by about 3.5 feet.

9. A method of treating a patient comprising a target, comprising:

placing the target in an electromagnetic field in an apparatus comprised of; a signal generator for producing a signal of predetermined amplitude and predetermined frequency, an attenuator connected to said generator for receiving said signal therefrom for driving helmholtz coils to which said attenuator is connected, and helmholtz coils connected to said attenuator for being driven thereby to generate said predetermined magnetic field; and generating and applying a magnetic field to said target by operating said apparatus in a manner to generate a field which matches the formula $mc^2=Bvlq$, wherein m equals a mass of one of a plurality of targets to which the field is to be applied, c equals the speed of light, v equals inertial velocity of said mass, l equals the length of the patient or portion thereof, and q equals unity of charge, to thereby derive a magnetic flux density (B).

10. The method of claim 9, further comprising: applying a field with multiple harmonic frequencies in the range of about DC to about 1000 Hz, and wherein said field is applied to therapeutically treat conditions comprised of one of virus infections, pathogenic organism infection, oncogenic abnormalities, infectious, immunogenic RNA or DNA, chronic pain and neurological disorders.

11. The method of claim 10, wherein said helmholtz coils comprise two coils spaced a predetermined distance apart, are about eighteen inches in diameter, and the method comprises applying said field with said coils on a patient or patient portion suffering pain.

12. The method of claim 10, wherein said helmholtz coils comprise two coils spaced a predetermined distance apart, are about seven feet in diameter, and the method comprises applying said field with said coils on a patient target having an infection.

13. The method of claim 10, wherein said helmholtz coils comprise two coils spaced a predetermined distance apart, are about seven feet in diameter, and the method comprises applying said field with said coils, on a patient target causing an oncogenic abnormality.

14. The method of claim 10, wherein said helmholtz coils comprise two coils spaced a predetermined distance apart, are about eighteen inches in diameter, and the method comprises applying said field with said coils on a patient or patient portion having a neurological disorder.

15. The method of claim 14, wherein said neurological disorder is multiple sclerosis.

16. The method of claim 14, wherein said neurological disorder is Alzheimer's.

17. The method of claim 14, wherein said neurological disorder is amytrophic lateral sclerosis.

18. The method of claim 14, wherein said neurological disorder is cerebral palsy.

19. An Apparatus for generating an electromagnetic field to be applied to a patient which comprises a target, for treating specified conditions, the apparatus comprising:

a signal generator for producing a signal of predetermined amplitude and predetermined frequency to generate a desired magnetic field which is produced by Helmholtz coils operatively connected thereto, said signal generator being set such that the field generated matches the formula $mc^2=Bvlq$, wherein m equals a mass of one of a plurality of targets to which the field is applied, c equals the speed of light, v equals inertial velocity of said mass, l equals the length of the patient or portion thereof, and q equals unity of charge, to thereby derive a magnetic flux density (B);

an attenuator connected for receiving said signal from said signal generator and to drive Helmholtz coils to which the attenuator is connected;

Helmholtz coils connected to said attenuator for being driven by said attenuator in a manner to generate said magnetic field; and a support stand for supporting said Helmholtz coils, and said Helmholtz coils numbering two and supported by said support stand in a location in relation to each other to allow subjecting of a target positioned between the coils to said desired magnetic field.

20. The apparatus of claim 19, wherein said support stand is constructed to allow 360° rotation of the coils, and vertical and horizontal movement of the coils.

21. A method of treating a patient which comprises a target, comprising:

placing the target in an electromagnetic field apparatus comprised of; a signal generator for producing a signal of predetermined amplitude and predetermined frequency, an attenuator connected to said generator for receiving said signal therefrom for driving Helmholtz coils to which said attenuator is connected, Helmholtz coils connected to said attenuator for being driven thereby to generate said predetermined magnetic field; a support stand for supporting said Helmholtz coils, and said Helmholtz coils numbering two and supported by said support stand in a location in relation to each other to allow subjecting of a target portioned between the coils to a desired magnetic field;

positioning the target between the coils; and generating and applying a magnetic field to the target by operating the apparatus in a manner to generate a field which matches the formula $mc^2=Bvlq$, wherein m equals a mass of one of a plurality of targets to which the field is to be applied, c equals the speed of light, v equals inertial velocity of said mass, l equals the length of the patient or portion thereof, and q equals unity of charge, to thereby derive a magnetic flux density (B).

\* \* \* \* \*